United States Patent [19]
Whisson

[11] Patent Number: 5,201,718
[45] Date of Patent: Apr. 13, 1993

[54] PARENTERAL DEVICE

[76] Inventor: Maxwell E. Whisson, 15 Loftus Street, Nedlands, Western Australia, Australia, 6009

[21] Appl. No.: 368,297

[22] PCT Filed: Apr. 15, 1988

[86] PCT No.: PCT/AU88/00111
§ 371 Date: Jun. 14, 1989
§ 102(e) Date: Jun. 14, 1989

[87] PCT Pub. No.: WO88/08315
PCT Pub. Date: Nov. 3, 1988

[30] Foreign Application Priority Data

Apr. 22, 1987 [AU] Australia .................................. PI1542
Aug. 18, 1987 [AU] Australia .................................. PI3749

[51] Int. Cl.$^5$ .............................................. A61M 5/32
[52] U.S. Cl. ...................................... 604/194; 604/195; 604/240
[58] Field of Search ............... 604/194, 195, 196, 218, 604/226, 239, 240, 221, 227

[56] References Cited

U.S. PATENT DOCUMENTS

| | | | |
|---|---|---|---|
| 2,752,919 | 7/1956 | Gabriel | 604/240 X |
| 2,833,280 | 5/1958 | Hein, Jr. | 604/195 X |
| 3,527,216 | 9/1970 | Snyder | 604/196 X |
| 3,548,626 | 6/1971 | Johannson | 128/218 |
| 4,316,463 | 2/1982 | Schmitz et al. | 604/194 X |

FOREIGN PATENT DOCUMENTS

| | | |
|---|---|---|
| 2119148 | 7/1948 | Australia . |
| 201484 | 2/1955 | Australia . |
| 164214 | 3/1955 | Australia . |
| 202213 | 5/1955 | Australia . |
| 232255 | 9/1959 | Australia . |
| 243057 | 6/1963 | Australia . |
| 57556 | 2/1971 | Australia . |
| 13731 | 10/1971 | Australia . |
| 83001091 | 4/1984 | PCT Int'l Appl. . |

Primary Examiner—C. Fred Rosenbaum
Assistant Examiner—Corrine Maglione
Attorney, Agent, or Firm—Eckert Seamans Cherin & Mellott

[57] ABSTRACT

A parenteral device (10) for the transfer of fluids to or from a living body. The device (10) comprises a body (11) having a chamber (18) and an opening (17) provided in the wall of the chamber (18). A hollow needle (19) is open at its outer end and is slidably mounted to the body (11) for axial movement therein. The needle (19) is movable between a first position in which it extends through said opening (17) such that its outer end extends beyond the body (11) and a second position in which the outer end of said needle is located innermost from said opening (17). A second aperture (21) in the wall of the needle (19) provides communication between the chamber (18) and the lumen of the needle (19) when in the first position.

11 Claims, 4 Drawing Sheets

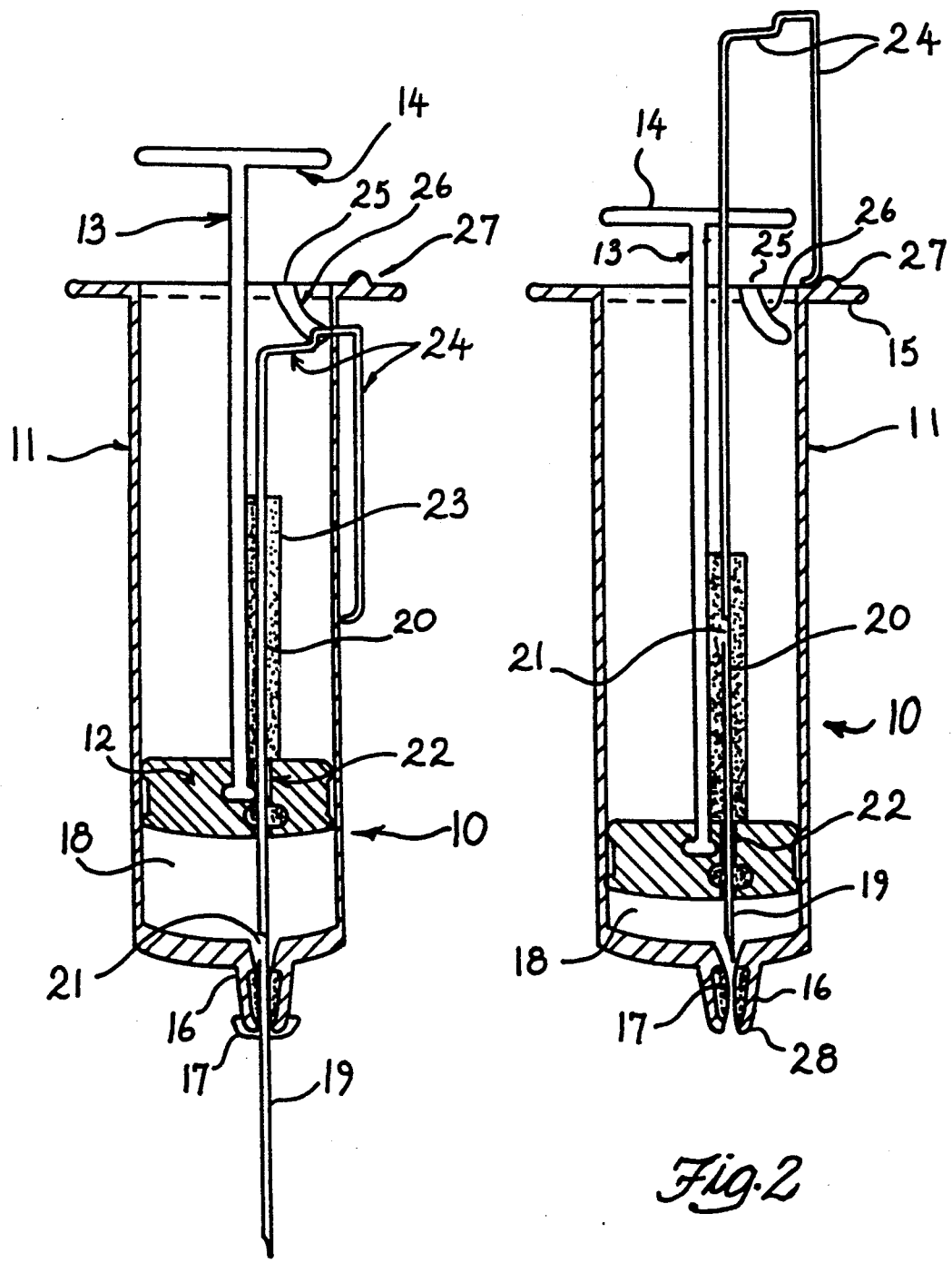

PARENTERAL DEVICE

This invention relates to a parenteral device for the transfer of fluids to, or from a living body.

Throughout this specification the term "parenteral device" shall be taken to include hypodermic syringes, cannulas and like devices which may be used for passively introducing or withdrawing fluids from a living body.

It is the primary characteristic of parenteral devices that a sharp hollow needle be provided to facilitate the transfer of fluids to, or from a body. The difficulty created by the presence of such a needle arises from the possibility of injury which may be caused to a user or clinician when using the device or any person who may be required to handle the device before or subsequent to use. It will be appreciated however that the dangers resulting from possible injury are surpassed by the dangers of infection that may arise from such injury due to the presence of the pathogens which may be present on the needle as a result of its usage. Furthermore this danger does not disappear at the conclusion of the utilization of the parenteral device but is always present while the device remain in existence which has resulted in very careful disposal procedures being adopted in institutions where such parenteral devices are used. Such precautions, however, are not necessarily adopted where parenteral devices are used in out-of-clinic situations such as instances where the user is required to inject themselves with a parenteral.

It is an object of this invention to provide a parenteral device which can reduce the possibility of injury and subsequent infection from a used device.

In one form the invention resides in a parenteral device comprising a hollow body having a wall which defines a chamber; a passageway formed through a portion of the wall, said portion of the wall being fixed in relation to the body; an opening provided at the outer end of the passageway; a needle body comprising a needle having a lumen, a first aperture at one end; the needle body being slidable within the body; a second aperture in the wall of the needle body which opens into the lumen of the needle; the needle body further comprising an axial extension supported from the other end of the hollow needle, said axial extension having a handle means to enable manual manipulation to effect the slidable movement of the needle body in the body; the needle body being slidable from a first position at which the one end of the needle extends through the passageway beyond the opening and at which the needle is sealingly received in the passageway; to a second position at which the one end of the needle is located inward from the opening; the needle body also being slidable from the second position to the first position; the second aperture in the wall of the needle body providing communication between the chamber and the lumen of the needle when the needle body is in the first position; and a seal provided between the body and the axial extension to slidably and sealingly engage the axial extension between the second aperture and the handle means.

The invention will be more fully understood in the light of the following description of one specific embodiment. The description is made with reference to the accompanying drawing of which:

FIG. 1 is a schematic side of a syringe according to the first embodiment having the needle in the first position;

FIG. 2 is a schematic sectional elevation of a syringe according to the first embodiment having the needle in a second position;

Figures 3, 4:
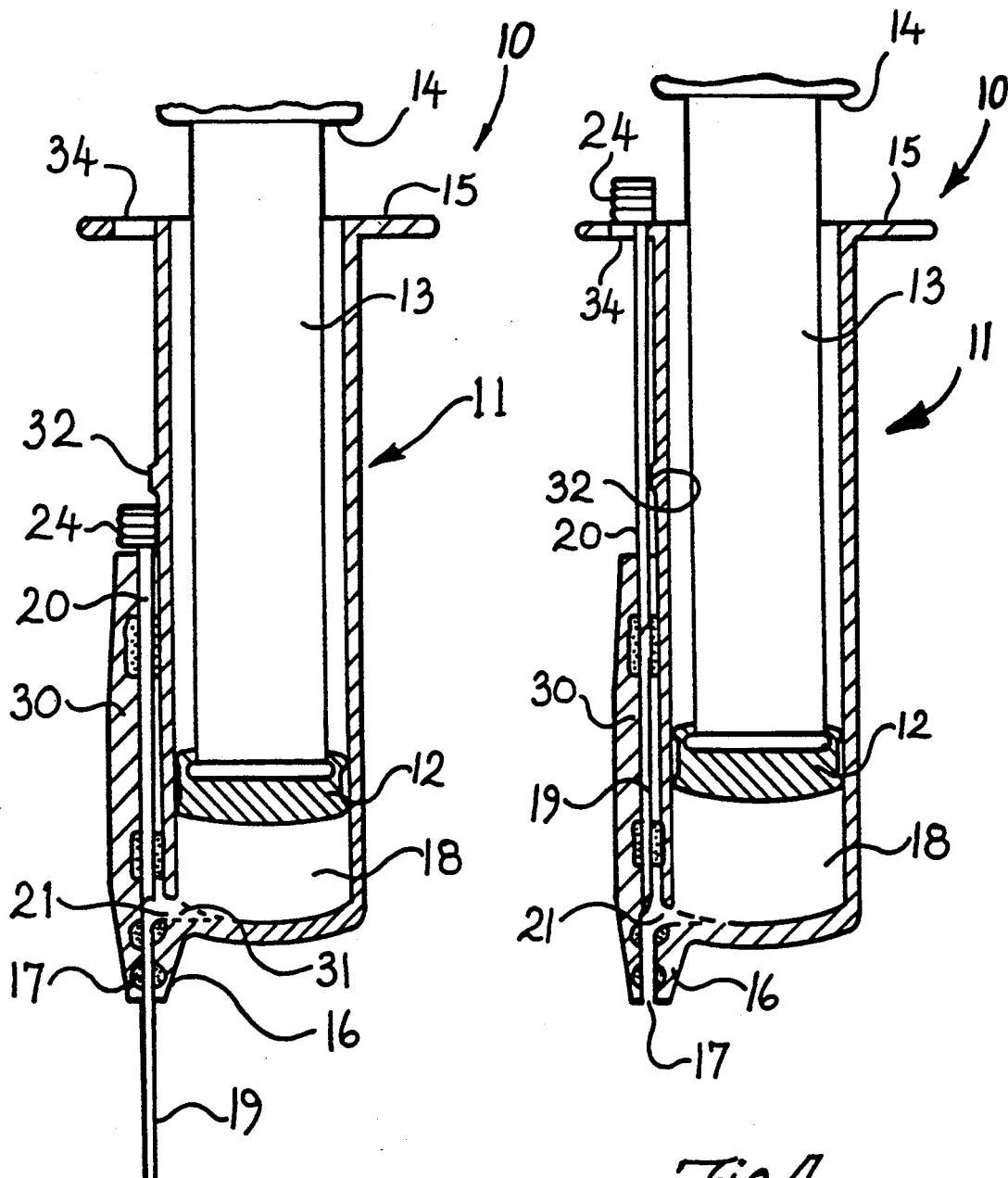
FIG. 3 is a sectional side elevation of a syringe according to the second embodiment having the needle in the first position.
FIG. 4 is a sectional side elevation of a syringe according to the second embodiment having the needle in the second position.

The first embodiment shown at FIGS. 1 and 2 comprises a hypodermic syringe 10 which can be used for the injection of parenteral into a living body or alternatively for removal of fluids from a body. The syringe comprises a substantially cylindrical body 11 which slidably and sealingly accommodates a piston 12 which is movable axially through the body 11 and is caused to move by means of a plunger rod 13 which extends from the open end of the body 11. The inner face of the body and piston may be of non-circular configuration to establish rotational stability of the piston in the body. The plunger rod 13 is provided at its outer end with an abutment 14 which together with a flange 15 provided at the outer end of the body 11 facilitates manipulation of the plunger and the movement of the piston by a user.

The other end of the body 11 is closed and is provided with an off center axially directed annular boss 16 having a passageway 17 which provides communication between the interior of the body 11 and the exterior. As the piston 12 is caused to move towards or away from the closed end, so the volume of a chamber 18 defined within the body between the piston 12 and the closed end is caused to vary. The boss 16 may have a suitable configuration in order to accommodate a "Luer" or like fitting which may be used to effect the transfer of parenteral into the chamber 18 from an ampoule or like container. Alternatively the boss 16 may be formed with a sharpened top and suitably shaped to be used to take up fluid from a sealed ampoule.

The piston 12 and plunger rod 13 slidably accommodate a hollow needle 19 which is mounted to one end of a control rod 20 whereby the needle 19 is movable axially in relation to the plunger rod 13 through the piston 12. The location of the needle is such that it is aligned with the passageway 17 in the boss 16 provided on the body 11 whereby on axial movement of the control rod 20 the needle 19 is movable through the passageway 17. The outer end of the hollow needle 19 is provided with an opening for the transfer of fluid out of the lumen of the needle while the inner end of the needle is provided with a laterally directed second opening 21. The axially directed passageway in the piston which accommodates the control rod 20 and needle 19 is provided with an appropriate sealing means to prevent leakage of fluid from the chamber 18 to the axial passageway 22. In addition, the plunger rod 13 supports a tubular sealing element 23 which slidably and sealingly accommodates the control rod 20 and needle 19 to further prevent any leakage from the chamber 18 and also to prevent contamination of the needle 19 when retracted and accommodated within the tubular support element 23. The outer end of the control rod 20 is provided with an overturned portion which is receivable in a radial slot 25 formed in the flange 15 of the body 11 and a downwardly oblique slot 26 formed in the body 11 and which is configured to facilitate retention of the downturned portion 24 of the control rod 23 in the body 11 on the location of the needle in its first position as shown at FIG. 1 at which it extends through the passageway 17 and the boss 16. On outward axial movement of the control rod 20 once disengaged from the slots 25 and 26 in the body 11 the lower end of the downturned portion 24 becomes engaged with the outer axial face of the flange 15 and a stop 27 provided thereon aid retain the control rod 23 at its outermost extension in relation to the body as shown at FIG. 2 at which position the needle 19 is in its second position whereby it is retracted into the body 11 and is clear of the passageway 17.

The axial movement of the control rod 20 and the needle 19 is independent of the axial movement of the plunger rod 13 whereby the needle 19 may be located in either its first position as shown at FIG. 1 or its second position as shown at FIG. 2 and the piston can be located at any position within the body 11 and moved within the body 11. Therefore when the needle 19 is in its second position at which it is retracted within the body 11 the boss 16 may be fitted with a "Luer" of like fitting for the introduction of a parenteral into a body 11 form an ampoule or like receptacle by operation of the plunger rod 13. Once filled with a parenteral the needle 19 may be moved to its first position after removal of the "luer" fitting for the administration of the parenteral. Subsequent to the administration of the parenteral the needle 19 is moved to its second position at which time the syringe can be safely discarded. If it is desired to prevent the inadvertent movement of the needle 19 beyond the body 11 of the syringe, the syringe or control rod may be deformed to prevent any further axial movement of the control rod 20 and the needle 19 in the body 11.

If desired the first embodiment may be modified whereby the needle 19 and boss 16 are located centrally in the piston and body 11 respectively.

The second embodiment shown at FIGS. 3 and 4 relates to a modified form of hypodermic syringe. The syringe 10 according to the embodiment comprises a substantially cylindrical secondary body 41 which is closed at one end and is open at the other end. The secondary body supports a piston 12 which is sealingly received within the secondary body 41 and is slidable axially therein. The piston 12 is associated with a plunger rod 13 which extends from the open end of the secondary body 41 and is associated with an enlarged end which together with an outwardly directed flange provided at the open end of the secondary body 41 facilitates manipulation of the plunger. The secondary body 41 is associated with a primary body 30 in the form of a tubular housing mounted on the exterior wall of the secondary body 41 where the axes of the bodies are substantially parallel. The lower end of the primary body 30 is formed with a boss 16 which extends beyond the lower end of the secondary body 41 which if desired may be configured to facilitate engagement with a "Luer" or like fitting as described in relation to the first embodiment. The boss 16 is formed with a passageway 17 which provides communication between the interior of the tubular housing and the exterior. A secondary passageway 31 is formed through the common wall of the primary and secondary bodies to provide communication between the interior of the primary body and the chamber 18 provided in the secondary body between the piston 12 and the closed end of the secondary body. The primary body 30 slidably accommodates a needle body which comprises a needle 19 which is mounted to the lower end of a control rod 20. The upper end of the control rod 20 extends beyond the upper end of the primary body 30. The secondary body 41 is provided with a stop member 32 which is intended to engage the upper end of the control rod 20 when the needle is in the first position extending from the boss 17 as shown at FIG. 3 to prevent inadvertent axial displacement of the needle into the primary body 30. The outer end of the needle 19 is provided with a first aperture to facilitate the flow of parenteral from the needle 19 when in use. The inner end of the needle 19 is provided with a laterally directed second aperture 21. When the needle 19 is in its first position at which it extends through the passageway 17 and from the boss 16 as shown at FIG. 3 the second aperture 21 in the needle communicates with the secondary passageway 31 provided in the common wall of the primary and secondary bodies to facilitate the flow of parenteral from the chamber 18 to the interior of the primary body and into the needle 19. Suitable seals are provided on the internal walls of the primary body 30 to either side of the secondary passageway 31 to prevent leakage of a parenteral between the walls of the primary body 30 and the needle 19 and control rod 20. Furthermore, the control rod 20 and needle may be provided with an external configuration to facilitate sealing with the internal walls of the primary body 30.

When the needle 19 is in its fully retracted position at which it is fully accommodated within the secondary housing 30 the enlarged upper end of teh control rod 20 extends through an aperture 34 provided in the flange 15 of the secondary body whereby it becomes lockingly engaged with aperture 34 to prevent inadvertent axial displacement of the needle and control rod from the second position as shown at FIG. 4.

It should be appreciated that any suitable form of retaining the control rod in either of its positions may be used. When in the second position the free end of the needle 19 is positioned clear of the passageway 17 and the boss 16. This facilitates the delivery of body fluids into a specimen receptacle or the drawing of parenteral into the chamber 18 from an ampoule or similar container.

in the case of both the first and second embodiments, the boss 16 may be configured to eliminate the need of a "Luer" fitting whereby the boss 16 may be inserted directly into an ampoule or container for the charging of the chamber 18 with parenteral.

In addition, in both the first and second embodiments, the needle when in second position need not be drawn clear of the passageway 17 within the boss 16. This ensures that the passageway 17 in the boss is closed by the needle and thus the chamber 18 is sealed with the needle in the retracted state.

This latter feature is of importance where the syringe is used to draw samples which are required to be stored in the syringe during transportation to a testing station or like or where the syringe is required to be supplied by the manufacturers in a condition where they are pre-filled with a parenteral.

In the case of the second embodiment, the secondary body 41 and/or primary body 30 and/or the control rod 20 may be such that they may be distorted on locating the needle 19 and control rod 20 in the second position to prevent any axial displacement of the needle from the used syringe.

In relation to the second embodiment the sealing provided between the needle 19 and the interior of the primary body 30 may be such that the flow of parenteral from the chamber 18 to the needle 19 may be shut off by rotating the needle 19 about its central axis.

Furthermore the secondary body 41 may be formed with two compartments which are each provided with their own piston and plunger but with a common primary body 30 whereby the chamber of each secondary body maybe brought into communication with the lumen of the needle by rotation of the needle within the primary body about its central longitudinal axis or alternatively by axial displacement of the needle within the primary body between one of the two positions. A further alternative may comprise the provision of a plurality of primary bodies 30 each accommodating their own retractable needle 19 and being capable of communicating with a common secondary body.

Figure 5:
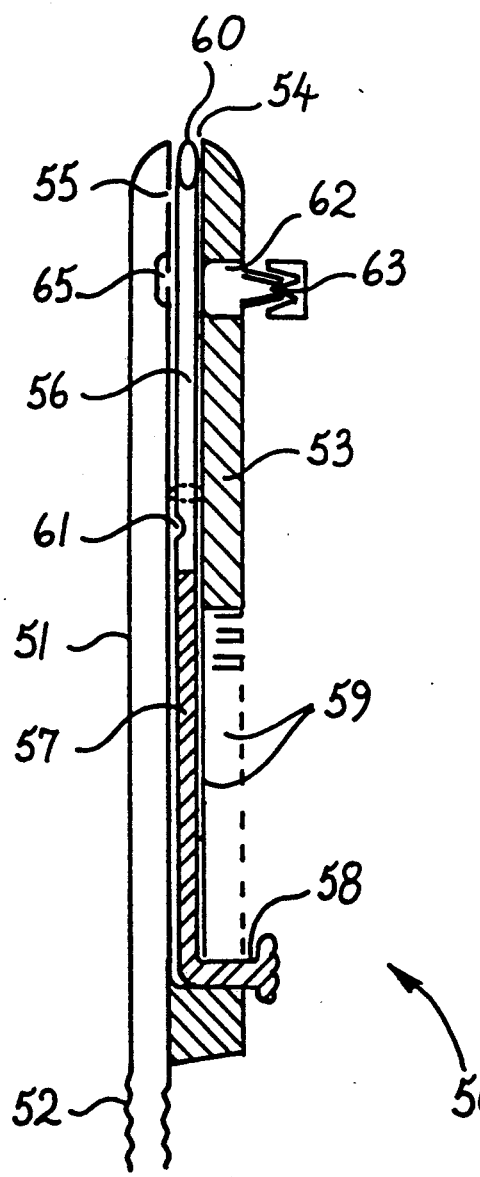
FIG. 5 is a sectional side elevation of a cannula according to the third embodiment having the needle in the second position.
Figure 6:
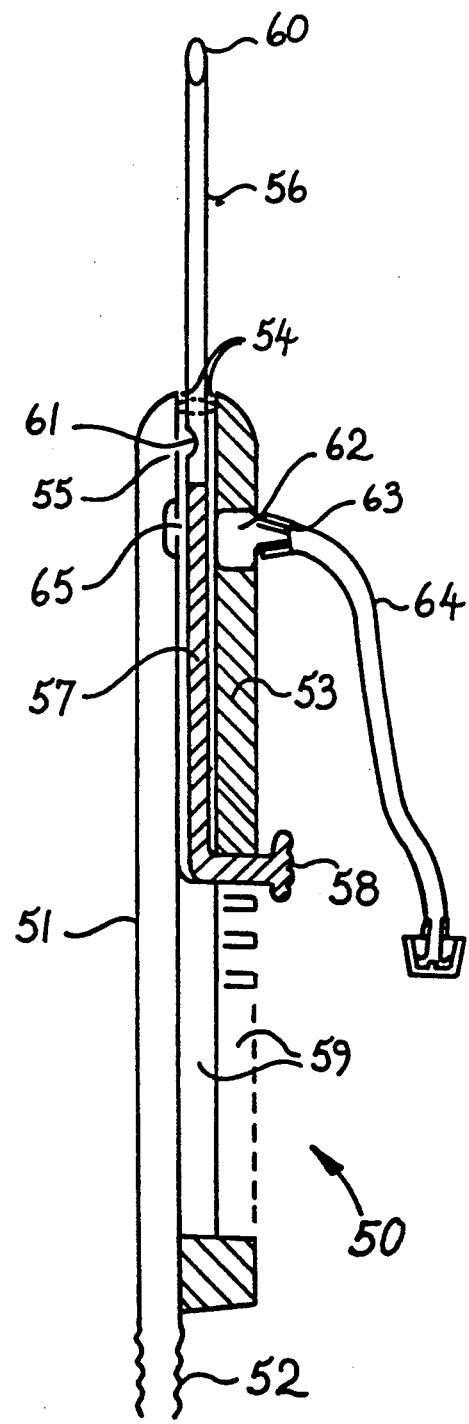
FIG. 6 is a sectional side elevation of the cannula of the third embodiment having the needle in the first position.

The third embodiment of FIGS. 5 and 6 relates to a cannula 50 which can be used for the passive extraction or administration of fluids to a living body. The cannula comprises a substantially tubular element 51 which is closed at one end and is adapted at the other end 52 to be connected to tubing which is associated with a receptacle containing a parenteral or which is intended to receive body fluids. The tubular element 51 is associated with an elongate hollow body 53 which is mounted to one side of the tubular element 51 in substantially parallel relationship therewith and which is provided with a passageway 54 at the end adjacent the closed end of the tubular element 51. The passageway 54 provides communication between the interior of the body 53 and the exterior. The common wall of the tubular element 51 and the body 53 is formed with a secondary passageway 55 adjacent the inner end of the passageway 54 in the body. The interior of the body 53 slidably supports a hollow needle 56 which is mounted to one end of a control rod 57. The control rod 57 is slidable within the body 53 and is provided at its innermost end with a laterally projecting protuberance 58 which is slidably receivable in an axial slot 59 provided in the wall of the body 53 to allow for axial displacement of the control rod 57 and consequently the needle 56 between a first position as shown at FIG. 6 at which the needle extends beyond the closed end of the body 53 and a second position as shown at FIG. 5 at which the needle is fully accommodated within the body 53. The hollow needle is provided with a first opening 60 at its outer end and a second opening 61 at or near its inner end which communicates with the secondary passageway 55 in the wall of the tubular element 51 when the needle is in its first position as shown at FIG. 6. Suitable sealing means are provided on the interior wall of the body 53 in the region of the secondary passageway 53 and or on the external face of the needle 56 in the region of the second aperture 61 to ensure there is no leakage of any fluids between the internal wall of the body 53 and the needle 56.

If desired the needle 56 and control rod 57 may be rotatable in the body 53 about the central longitudinal axis of the needle 56 and the seal provided between the interior wall of the body 53 and the needle 56 may be such that with rotation of the needle the second aperture therein may be brought into and out of communication with the secondary passageway 55 to allow a flow of fluid therebetween and/or prevent such fluid flow. In addition, the slidable relationship between the protuberance 58 on the control rod 57 within the slot 59 may be such that the needle is retained in either of its end positions to prevent inadvertent displacement form either position. Furthermore, the body of the cannula may be formed of a material which facilitates the permanent distortion of the tubular element 51 when the needle 19 is in its retracted position and which prevents displacement of the needle from a used cannula.

The cannula of the embodiment shown at FIGS. 5 and 6 incorporates a feature which may be preferred however which is not essential. The feature comprises an annular chamber 62 at a position spaced from the closed end of the tubular element 51 which is provided with an opening 63 which can be connected to tubing 64. The annular chamber 62 is provided with a third passageway 65 which opens into the interior of the body 53 and which can be brought into communication with the second opening 61 provided in the needle 19. Suitable indexing is provided on the slot 59 to ensure retention of the control rod 57 at a position at which such communication can be provided. The function of the annular chamber is to provide for an alternative admission of a second fluid into a body or alternatively the extraction of body fluids prior to or subsequent to the administration of a parenteral, or alternatively sampling of fluids which have been discharged through the tubular element 51 of the cannula.

Figure 7:
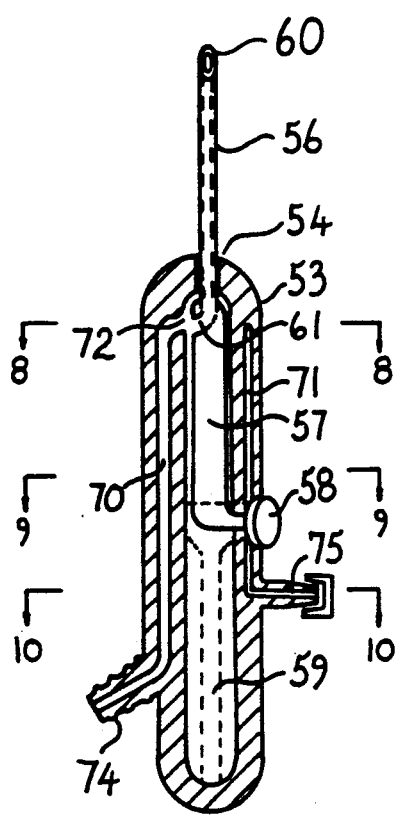
FIG. 7 is a sectional side elevation of a cannula according to the fourth embodiment.
Figure 8:
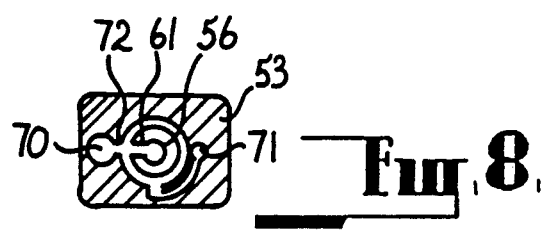
FIG. 8 is a cross-sectional view of the fourth embodiment of FIG. 7 along line 8—8.
Figure 9:
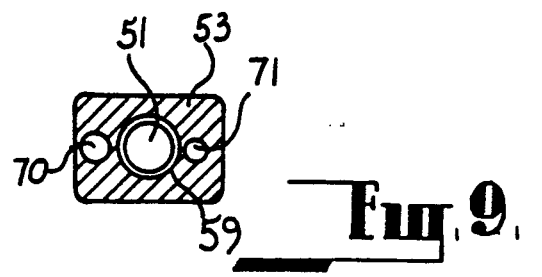
FIG. 9 is a cross-sectional view of the fourth embodiment along line 9—9.
Figure 10:
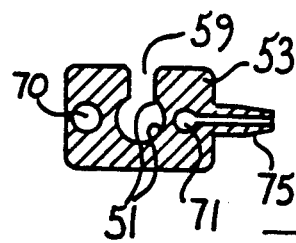
FIG. 10 is a cross-sectional elevation of the fourth embodiment along line 10—10.

The fourth embodiment shown at FIGS. 6, 7, 8, 9 and 10 is also directed to a cannula. The cannula of the fourth embodiment comprises a hollow elongate body 53 which slidably receives a control rod 57 having a hollow needle 56 mounted to one end thereof which is movable through a passageway 54 provided in one end of the body 53. The side walls of the tubular body 51 are provided with two separate fluid flow ducts 70 and 71 which open into the interior of the body 53 through separate secondary passageways 72 and 73 which are angularly displaced from each other about a central longitudinal axis and each of which are provided with their own outlet and or inlet 74 and 75. The needle 56 is provided at its outer end with a first aperture 60 and at its inner end with a second laterally opening aperture 61. The control rod 57 is provided with a laterally extending portion 58 which extends through axial slot 59 provided in the side wall of the body 53. At the end of the slot 59, corresponding to the position at which the needle is in its first position as shown at FIG. 7 where it extends beyond the passageway 54 in the body 53 and the second aperture 61 in the needle is brought into communication with either secondary passageway 72 or 73 of either duct 70 or 71 respectively by rotation of the control rod 57. This is achieved by means of a circumferential slot provided in the end of the axial slot 59 (not shown) which permits rotation of the protuberance 58.

By means of the fourth embodiment the cannula maybe used to service two different purposes without the need for replacing the cannula by another to facilitate an exchange of such purposes.

It should be appreciated that each of the embodiments may be modified whereby the needle of each is spring biased to either its first or second position and is associated with a latching means whereby on release of the latching means the needle will move under the influence of the spring pressure to its first or second position respectively.

Each of the embodiments described above provide a parenteral device whereby the exposure of the needle can be minimized during use and disposal without the need for a needle cap and which can reduce the need for special disposal procedures previously required of the needle of such devices.

It should be appreciated that the scope of the present invention need not be limited to the particular scope of the embodiment described above.

I claim:

1. A parenteral device comprising a hollow body having a wall which defines a chamber; a passageway formed through a portion of the wall, said portion of the wall being fixed in relation to the body; an opening provided at the outer end of the passageway; a needle body comprising a needle having a lumen, a first aperture at one end; the needle body being slidable within the body; a second aperture in the wall of the needle body which opens into the lumen of the needle; the needle body further comprising an axial extension supported from the other end of the hollow needle, said axial extension having a handle means to enable manual manipulation to effect the slidable movement of the needle body in the body; the needle body being freely slidable via the handle from a first position at which the one end of the needle extends through the passageway beyond the opening and at which the needle is sealingly received in the passageway, the needle extending through the passageway; to a second position at which the one end of the needle is located inward from the opening; the needle body also being freely slidable vie the handle from the second position to the first position; the second aperture in the wall of the needle body providing communication between the chamber and the lumen of the needle when the needle body is in the first position; and a seal provided between the body and the axial extension to slidably and sealingly engage the axial extension between the second aperture and the handle means.

2. A parenteral device as claimed at claim 1 wherein when the needle body is in its second position the first aperture is in direct communication with the chamber.

3. A parenteral device as claimed at claim 1 wherein a releasable retention means is provided to retain the needle body in its first position or in its second position.

4. A parenteral device as claimed at claim 1 wherein the portion of the wall is formed as a tubular boss on the body, the exterior side walls of the boss having a tapered configuration.

5. A parenteral device as claimed at claim 4 wherein the boss has a sharpened end.

6. A parenteral device comprising a hollow body having a wall which defines a chamber; a passageway formed through a portion of the wall, said portion of the wall being fixed in relation to the body; an opening provided at the outer end of the passageway; a needle body comprising a needle having a lumen, a first aperture at one end; the needle body being slidable within the body; a second aperture in the wall of the needle body which opens into the lumen of the needle; the needle body further comprising an axial extension supported from the other end of the hollow needle, said axial extension having a handle means to enable manual manipulation to effect the slidable movement of the needle body in the body; the needle body being slidable from a first position at which the one end of the needle extends through the passageway beyond the opening and at which the needle is sealing received in the passageway, the needle extending through the passageway; to a second position at which the one end of the needle is located inward from the opening; the needle body also being slidable from the second position to the first position; the second aperture in the wall of the needle body providing communication between the chamber and the lumen of the needle when the needle body is in the first position; and a seal provided between the body and the axial extension to slidably and sealingly engage the axial extension between the second aperture and the handle means; wherein said body comprises a syringe having a piston slidably accommodated within the body, and wherein movement of the piston and manipulated of the needle via said handle means are independent of one another.

7. A parenteral device as claimed at claim 6 wherein the needle body is slidably accommodated by a tubular seal associated with the piston and which accommodates a portion of the hollow needle when in the second position.

8. A parenteral device as claimed at claim 6, wherein the axial extension of the needle is slidably and sealing received by the piston.

9. A parenteral device comprising a hollow body having a wall which defines a chamber; a passageway formed through a portion of the wall, said portion of the wall being fixed in relation to the body; an opening provided at the outer end of the passageway; a needle body comprising a needle having a lumen, a first aperture at one end; the needle body being slidable within the body; a second aperture in the wall of the needle body which opens into the lumen of the needle; the needle body further comprising an axial extension supported from the other end of the hollow needle, said axial extension having a handle means to enable manual manipulation to effect the slidable movement of the needle body in the body; the needle body being freely slidable via the handle from a first position at which the one end of the needle extends through the passageway beyond the opening and at which the needle is sealingly received in the passageway, the needle extending through the passageway; to a second position at which the one end of the needle is located inward from the opening; the needle body also being freely slidable via the handle from the second position to the first position; the second aperture in the wall of the needle body providing communication between the chamber and the lumen of the needle when the needle body is in the first position; and a seal provided between the body and the axial extension to slidably and sealing engage the axial extension between the second aperture and the handle means, and wherein the needle is sealing engaged int he passageway inward of the opening when the needle body is in the second position to sealing close the chamber.

10. A parenteral device as claimed at claim 9, wherein the needle body is movable to and from a third position inward of the second position at which the one end of the needle is not sealingly engaged in the passageway.

11. A parenteral device comprising a hollow body having a wall which defines a chamber; a passageway formed through a portion of the wall, said portion of the wall being fixed in relation to the body; an opening provided at the outer end of the passageway; a needle body comprising a needle having a lumen, a first aperture at one end; the needle body being slidable within the body; a second aperture in the wall of the needle body which opens into the lumen of the needle; the needle body further comprising an axial extension supported from the other end of the hollow needle, said axial extension having a handle means to enable manual manipulation to effect the slidable movement of the needle body in the body; the needle body being freely slidable via the handle from a first position at which the one end of the needle extends through the passageway beyond the opening and at which the needle is sealingly received in the passageway, the needle extending through the passageway; to a second position at which the one end of the needle is located inward from the opening; the needle body also being freely slidable via the handle from the second position to the first position; the second aperture in the wall of the needle body providing communication between the chamber and the lumen of the needle when the needle body is in the first position; and a seal provided between the body and the axial extension to slidably and sealingly engage the axial extension between the second aperture and the handle means, and wherein said body comprises a syringe having a piston slidably accommodated within the body, said axial extension being slidably and sealingly received by the piston.

* * * * *

UNITED STATES PATENT AND TRADEMARK OFFICE
CERTIFICATE OF CORRECTION

PATENT NO. : 5,201,718
DATED : April 13, 1993
INVENTOR(S) : Maxwell E. WHISSON

It is certified that error appears in the above-identified patent and that said Letters Patent is hereby corrected as shown below:

On the title page: Item [30]:
In the Foreign Application Priority Data, the priority date of "Aug. 18, 1987" should read --Aug. 14, 1987--.

Column 1, line 25, "remain" should read --remains--.

Column 3, line 23, insert --to-- after there on and delete "aid".

Column 3, line 38, change "form" to --from--.

Column 3, line 41, change "luer" to --Luer--.

Column 4, line 44, change "teh" to --the--.

Column 4, line 58, change "in" to --In--.

Column 7, line 40, change "vie" to --via--.

Column 8, line 9, change "sealing" to --sealingly--.

Column 8, lines 22 and 23, change "manipulated" to --manipulation--.

Column 8, line 31, change "sealing" to --sealingly--.

Column 8, line 59, change "sealing" to --sealingly--.

Column 8, line 61, change "sealing" to --sealingly--.

Column 8, line 61, change "int he" to --in the--.

UNITED STATES PATENT AND TRADEMARK OFFICE
CERTIFICATE OF CORRECTION

PATENT NO. : 5,201,718
DATED : April 13, 1993
INVENTOR(S) : Maxwell E. Whisson

It is certified that error appears in the above-indentified patent and that said Letters Patent is hereby corrected as shown below:

Column 8, line 63, change "sealing" to --sealingly--.

Cancel Figs. 3 and 4, and insert the Figs. 3 and 4 substituted below:

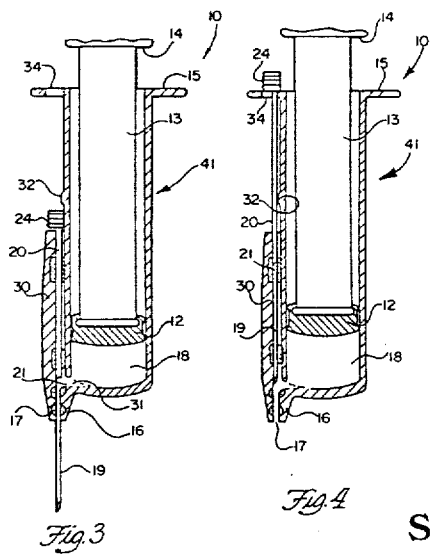

Fig. 3   Fig. 4

Signed and Sealed this

Twenty-fifth Day of January, 1994

Attest:

BRUCE LEHMAN

Attesting Officer

Commissioner of Patents and Trademarks